United States Patent [19]
Hossain et al.

[11] Patent Number: 6,005,915
[45] Date of Patent: Dec. 21, 1999

[54] APPARATUS AND METHOD FOR MEASURING THE ROUGHNESS OF A TARGET MATERIAL SURFACE BASED UPON THE SCATTERING OF INCIDENT X-RAY PHOTONS

[75] Inventors: Tim Z. Hossain; Donald A. Tiffin; Joel R. Stanford, all of Austin, Tex.

[73] Assignee: Advanced Micro Devices, Inc., Sunnyvale, Calif.

[21] Appl. No.: 08/966,158

[22] Filed: Nov. 7, 1997

[51] Int. Cl.$^6$ .................................................. G01N 23/201
[52] U.S. Cl. ............................................. 378/86; 378/70
[58] Field of Search ........................................ 378/86–90

[56] References Cited

U.S. PATENT DOCUMENTS

| | | |
|---|---|---|
| 3,688,110 | 8/1972 | Severance . |
| 3,859,525 | 1/1975 | Ashe . |
| 4,131,794 | 12/1978 | Brunix . |
| 4,764,945 | 8/1988 | Tadahiro . |
| 4,819,256 | 4/1989 | Annis . |
| 5,025,145 | 6/1991 | Lagowski . |
| 5,029,337 | 7/1991 | MacKenzie . |
| 5,220,591 | 6/1993 | Ohsugi et al. . |
| 5,274,688 | 12/1993 | Grodzins . |
| 5,325,416 | 6/1994 | Saito et al. . |
| 5,430,786 | 7/1995 | Komatsu et al. . |
| 5,471,293 | 11/1995 | Lowell et al. . |
| 5,537,451 | 7/1996 | Serebryakov et al. . |
| 5,657,363 | 8/1997 | Hossain . |
| 5,740,226 | 4/1998 | Komiya et al. ............................ 378/89 |
| 5,742,658 | 4/1998 | Tiffin et al. . |
| 5,778,039 | 7/1998 | Hossain et al. . |

OTHER PUBLICATIONS

Strobel, Howard A. et al., *Chemical Instrumentation: A Systematic Approach*, 1989 by John Wiley & Sons, Inc., pp. 723–777.

Lagowski et al., "Non–Contact Mapping of Heavy Metal Contamination for Silicon IC Fabrication," 1992, pp. A185–A192.

Moore, "Theory and Experiment on the Surface–Photovoltage Diffusion–Length Measurement as Applied to Amorphous Silicon," *American Institute of Physics*, 1983, pp. 222–228.

Nomura, et al. "Advances in X–Ray Analysis", (1989) vol. 32, pp. 205–210.

(List continued on next page.)

*Primary Examiner*—Craig E. Church
*Attorney, Agent, or Firm*—Kevin L. Daffer; Conley, Rose & Tayon

[57] ABSTRACT

An apparatus and method are present which use X-ray fluorescence techniques to determine the roughness of a target surface. The apparatus includes an X-ray source and an X-ray detector. The X-ray source produces primary X-ray photons formed into a primary X-ray beam, and the primary X-ray beam is directed to and incident upon the target surface. The X-ray detector is positioned to receive primary X-ray photons scattered by the target surface. A fraction of the primary X-ray photons scattered by the target surface is directly proportional to the roughness of the target surface. The roughness of the target surface is determined from the number of primary X-ray photons scattered by the target surface and received by the X-ray detector within a predetermined exposure time. The X-ray detector produces an output signal proportional to the energy levels of received X-ray photons. An energy range of interest is divided into segments. A computer system receives the X-ray detector output signals and increments corresponding counts associated with segments of the energy range of interest. Following exposure, the computer system produces a graph of the counts associated with each segment. The computer system also reviews the counts associated with a peak in the graph corresponding to the energy levels of the scattered primary X-ray photons, determines selected characteristics of the peak (e.g., a maximum count associated with the peak, the area under the peak, etc.), and uses calibration data to compute a surface roughness value.

24 Claims, 5 Drawing Sheets

OTHER PUBLICATIONS

Kosonocky, et al. "Electron. Des.", (Apr. 12, 1975), vol. 23, pp. 58–63.

Janesick, et al. "Optical Engineering", (Aug. 1987), vol. 26, No. 8, pp. 692–714.

Bower, "CCD—Solid State Imaging Technology," (1982 Catalog), pp. 121–125.

Amelio, "CCD—Solid State Imaging Technology," (1982 Catalog), pp. 126–1375.

LaVoie, M.A., et al, "Total reflection x–ray fluorescence analysis of planarized semiconductor product wafers," J. Vac. Sci. Technol. A 14(3), May/Jun. 1996, 3 pages.

Diebold, Alain C., "Calibration issues for total reflection x–ray fluorescence analysis of surface metallic contamination on silicon," J. Vac. Sci. Technol. A 14(3), May/Jun. 1996, 5 pages.

Strobel, Howard A. et al., *Chemical Instrumentation: A Systematic Approach*, 1989 by John Wiley & Sons, Inc., pp. 780–817.

Michette, Alan G., *Optical System For soft X Rays*, 1986 by Plenum Press, pp. 1–35.

IBM Corporation, "Total Reflection X–Ray Fluorescence Spectrometry (TXRF)," Printed from Internet May 19, 1998, 2 pages; "Charles Evan & Associates—Specialists in Materials Characterization—Detection Limit vs. Lateral Resolution," Printed from the Internet May 19, 1998, 1 page.

Taylor, Larry R. et al., *Instrumental Methods for Determining Elements*, 1994 by VCH Publishers, Inc., pp. 211–261.

Siemans energy & Automation, Inc., Analytical Instrumentation, "Direct–Drive Rotating Anode X–ray Generator," Printed from Internet May 19, 1998, 4 pages; "FR591 Rotating Anode Generator" Printed from Internet May 19, 1998, 1 page.

"X–Ray Tube Anatomy—Anode Target"; "X–Ray Tube Anatomy—Anode Shaft,"; "X–Ray Tube Anatomy—Anode Rotor,"; "X–Ray Tube Anatomy—Anode Portion of the Tube,"; "X–Ray Tube Anatomy—Filament Circuitry,"; Printed from the Internet May 19, 1998, 10 pages.

"Simultix 10/11 Rigaku/Multichannel Simultaneous X–ray Spectometer System" Printed from Internet May 19, 1998, 3 pages; "Simultix 10S, Simultix 11S," Printed from the Internet May 19, 1998, 4 pages.

"Improvement of Manufacturing Techniques Using Silicon Wafer," Nov. 10, 1995, 1 page; "Charles Evans & Associates—Specialists in Materials characterization—Summary Table of Surface Analytical Techniques," 3 pages; "XRF Analytical Methods at Northwest Research," 3 pages, ALS New vol. 11, Jan. 31, 1995, 3 pages.

APPARATUS AND METHOD FOR MEASURING THE ROUGHNESS OF A TARGET MATERIAL SURFACE BASED UPON THE SCATTERING OF INCIDENT X-RAY PHOTONS

BACKGROUND OF THE INVENTION

1. Field of the Invention

This invention relates to integrated circuit manufacturing and more particularly to determining the roughness of a surface of a target material.

2. Description of the Relevant Art

High quality gate oxides are essential to the manufacture of MOS transistors with stable and reliable operating characteristics. A layer of an electrical insulating material separates a gate electrode of a metal oxide semiconductor (MOS) transistor from an underlying substrate channel region between a source region and a drain region. This insulating layer is commonly made of silicon dioxide (oxide), and the oxide insulating layer is called a gate oxide. A voltage applied to the gate electrode in excess of a minimum "threshold" level attracts enough electrical charges into the channel region to form a conducting path between the source and drain regions.

In order to increase the current sourcing and sinking abilities (i.e., current drives) of MOS transistors, gate oxides are typically made as thin as possible. As the strength of the electric field developed between the gate electrode and the underlying substrate channel region and within the gate oxide is inversely proportional to the thickness of the gate oxide, thinner gate oxides must withstand higher electric field strengths. The maximum electric field strength a gate oxide can withstand before destructively breaking down depends upon the thickness of the gate oxide and the quality of the gate oxide. Thus thinner gate oxides must be of higher quality.

Electrical "oxide rupture" or "rupture voltage" measurements are often performed upon test structures (i.e., MOS capacitor structures) fabricated upon wafers in order to determine gate oxide quality. An oxide layer to be analyzed is formed on an upper surface of a semiconductor substrate, and an electrode is formed on an upper surface of the oxide layer. During rupture voltage testing, a voltage applied to the electrode is continually increased until the oxide is physically destroyed (i.e., "ruptures") and current flows freely from the electrode to the underlying substrate. The maximum applied voltage (i.e., electric field strength) that the oxide can withstand before breakdown is a function of the oxide thickness and quality.

Figure 1:
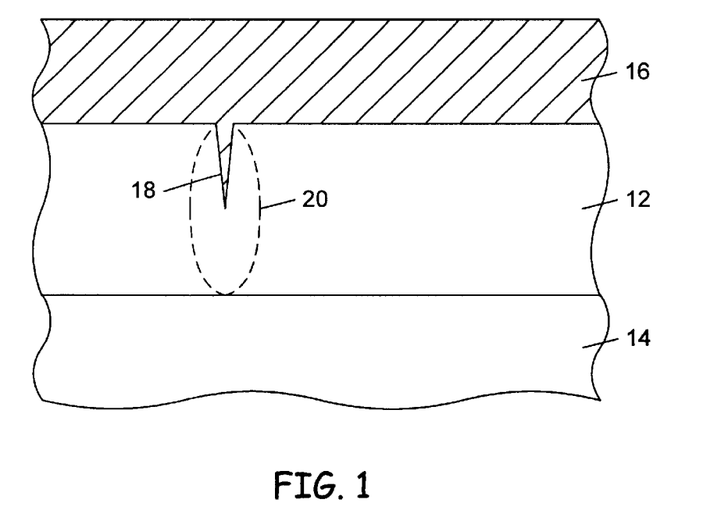
FIG. 1 is a partial cross-sectional view of a metal oxide semiconductor (MOS) capacitor structure, wherein the MOS capacitor structure includes an oxide layer formed upon an upper surface of a semiconductor substrate and an electrode formed upon an upper surface of the oxide layer, and wherein the oxide layer includes a pinhole defect in the upper surface.

"Pinhole" defects in oxides can cause unacceptably low oxide breakdown voltage levels (i.e., electric field strengths). FIG. 1 is a partial cross-sectional view of an MOS capacitor structure 10. MOS capacitor structure 10 includes an oxide layer 12 formed upon an upper surface of a semiconductor substrate 14, and an electrode 16 formed upon an upper surface of oxide layer 12. Oxide layer 12 is shown to include a pinhole defect 18 in the upper surface of oxide layer 12. Pinhole defect 18 is filled with the conductive material of electrode 16 when electrode 16 is formed. The thickness of oxide layer 12 is reduced in region 20 surrounding pinhole defect 18. During rupture voltage testing, the strength of the electric field between electrode 16 and substrate 14 within oxide layer 12 is greatest in region 20, and oxide layer 12 is more likely to fail first in region 20. The presence of pinhole defect 18 is thus likely to result in a measured breakdown voltage that is lower than expected.

Pinhole defects may be identified in very small "sample" regions of an upper surface of an oxide layer using microscopy. One such method is atomic force microscopy (AFM). AFM allows an area about 10 microns square to be viewed for the presence of pinhole defects. The equipment needed to perform AFM is, however, large and expensive, and studying a sufficient portion of an upper surface of an oxide layer in order to determine the number of pinhole defects present per unit of surface area would be time consuming. Thus AFM cannot be used efficiently in a manufacturing environment subject to volume production.

Oxide surfaces having few pinhole defects tend to be smooth, and oxide surfaces having a large number of pinhole defects per unit of surface area tend to be rough. Thus a measurement of the roughness of the upper surface of an oxide layer reflects the number of pinhole defects per unit of surface area (i.e., the quality of the oxide layer). It would thus be desirable to have a surface roughness measurement technique which is relatively fast and inexpensive, does not involve physical contact with structures on wafers (i.e., non-contact), and also does not result in the destruction of a specimen (i.e., non-destructive). Such a technique could be used to determine the qualities of oxides formed upon product wafers (i.e., wafers expected to yield operational integrated circuits), and would be well suited for use in a high-volume manufacturing environment.

X-ray fluorescence (XRF) spectroscopy techniques are commonly used to determine the elemental compositions of materials. In semiconductor manufacturing applications, a beam of primary X-ray photons is directed at the surface of a semiconductor wafer, and the energy levels (or corresponding wavelengths) of resultant secondary X-ray photons emitted by atoms of elements on and just under the surface of the wafer are measured. Atoms of elements in target materials emit secondary X-ray photons with uniquely characteristic energy levels (or corresponding wavelengths). Thus the elemental compositions of materials on and just under the surface of the wafer may be determined from the measured energy levels (or wavelengths) of emitted secondary X-ray photons. XRF spectroscopy techniques offer rapid, non-contact, non-destructive determination of elemental composition down to trace quantities over a wide range of elements with no sample preparation, and is thus a highly desirable tool for in-line product wafer examination.

Figure 2:
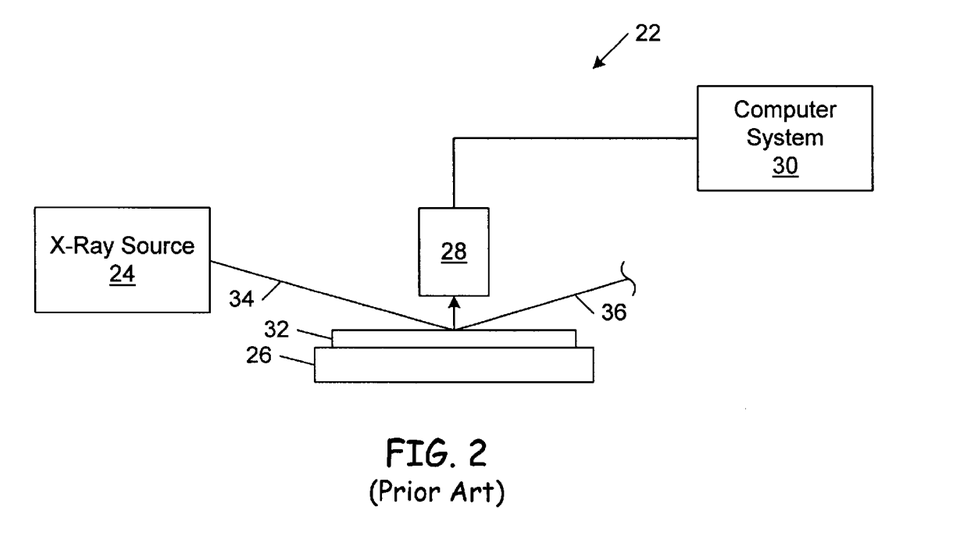
FIG. 2 is a side elevation view of a typical X-ray fluorescence (XRF) spectroscopy apparatus used to identify atoms of elements upon and just under a frontside surface of a semiconductor wafer, wherein a portion of the frontside surface of the semiconductor wafer is subjected to primary X-ray photons during analysis.

FIG. 2 is a side elevation view of a typical XRF spectroscopy apparatus 22. Apparatus 22 includes a high-power X-ray source 24, a sample stage 26, an X-ray detector 28, and a computer system 30. A planar backside surface of a semiconductor wafer 32 is placed on a flat upper surface of a sample stage 26, allowing a planar frontside surface of semiconductor wafer 32 to be subjected to primary X-ray photons during analysis. X-ray source 24 must be a high-power X-ray source in order to produce a relatively large number of X-ray photons per unit time. X-ray source 24 produces a beam of primary X-ray photons 34. The X-ray photons making up primary X-ray beam 34 strike the frontside surface of semiconductor wafer 32 within an exposed region, and have sufficient energy (i.e., sufficiently short wavelengths) to cause atoms of elements of interest located on and just under the surface of semiconductor wafer 32 to emit secondary X-ray photons. A portion of the X-ray photons making up primary X-ray beam 34 and striking the frontside surface of semiconductor wafer 32 are reflected away from the surface, forming a reflected primary X-ray beam 36.

Figure 3:
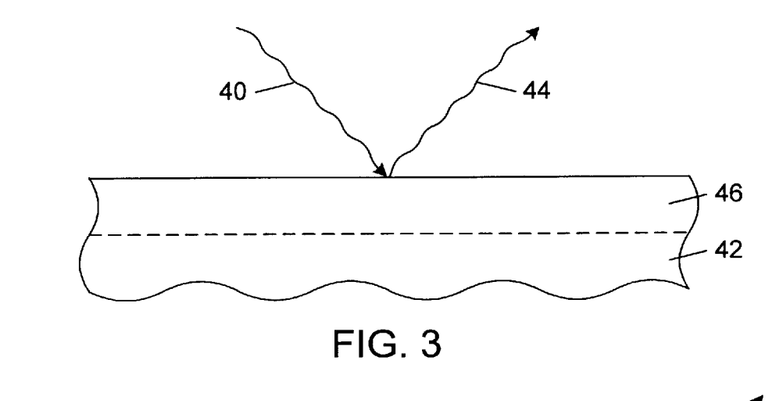
FIG. 3 is a side elevation view of a primary X-ray photon incident upon a target material, resulting in the emission of a secondary X-ray photon by the target material.
Figure 4A:
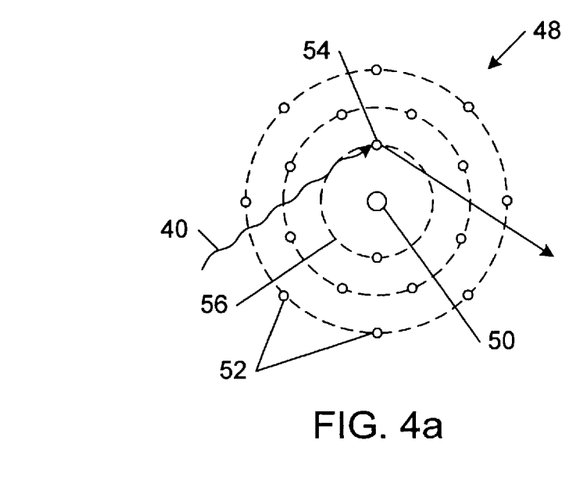
FIG. 4a is a representation of an atom of the target material of FIG. 3, wherein the primary X-ray photon is incident upon the atom, and wherein the entire energy of the primary X-ray photon is absorbed by the atom, resulting in the ejection of an electron in a "K" shell from the atom.
Figure 4B:
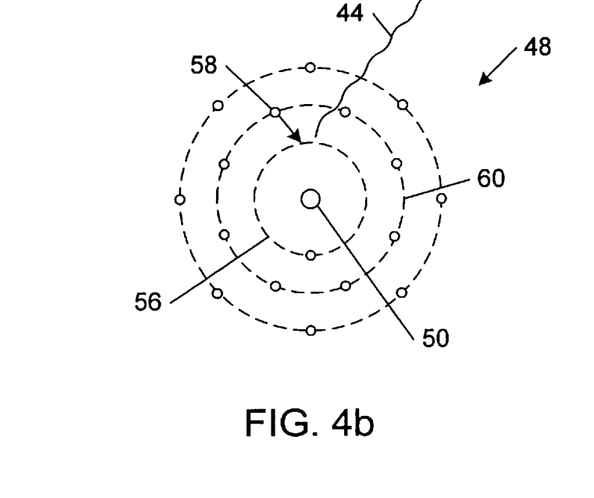
FIG. 4b is a representation of the atom of FIG. 4a following ejection of the K-shell electron, wherein an electron in an "L" shell of the atom fills the vacancy in the K shell, and wherein the atom simultaneously emits a secondary X-ray photon.

Atoms of elements on and just under the exposed region of the frontside surface of semiconductor wafer 32 absorb a fraction of the incident primary X-ray photons and emit characteristic secondary X-ray photons. FIGS. 3, 4a, and 4b will be used to describe this phenomenon. FIG. 3 is a side elevation view of a primary X-ray photon 40 incident upon a target material 42, resulting in the emission of a secondary X-ray photon 44 by target material 42. X-ray photon absorption and emission occur at the atomic level. XRF spectrometry permits examination of target material 42 from the surface of the target material down to a maximum escape depth 46 of secondary X-ray photons.

FIG. 4a is a representation of an atom 48 of target material 42. In the simple atomic model shown, atom 48 has a nucleus 50 surrounded by electrons 52 at different discrete distances from nucleus 50 called electron shells. A given electron shell has a binding energy level equal to the amount of energy required to remove an electron from the electron shell. The binding energy level of an electron shell is inversely proportional to the distance of the electron shell from the nucleus. The innermost electron shell of an atom is called the K shell, and has the highest binding energy level associated with it. In FIG. 4a, K-shell electron 54 is located in K shell 56.

FIG. 4a also shows primary X-ray photon 40 impacting atom 48 within target material 42. If the energy level of primary X-ray photon 40 (E) is greater than the binding energy level of a K shell 56 ($\phi_K$), the entire energy of primary X-ray photon 40 is absorbed by atom 48, and one of the electrons in K shell 56 is ejected from atom 48. As depicted in FIG. 4a, K-shell electron 54 is ejected from atom 48 after primary X-ray photon 40 is absorbed by atom 48. K-shell electron 54 is ejected with a kinetic energy of $(E-\phi_K)$.

With a vacancy in K shell 56, atom 48 is energetic and unstable. The most probable stabilization mechanism is the filling of the vacancy in K shell 56 by an electron located in an electron shell with a lower binding energy level. As shown in FIG. 4b, an L-shell electron 58 in L shell 60, farther from nucleus 50 than K shell 56, may fill the vacancy in K shell 56. As L-shell electron 58 fills the vacancy in K shell 56, atom 48 simultaneously emits secondary X-ray photon 44 with energy $(\phi_K-\phi_L)$. where $\phi_l$ is the binding energy level of L shell 60. With a vacancy now in L shell 60, ionized atom 48 is more stable and less energetic. The energy levels (or corresponding wavelengths) of secondary X-ray photons emitted by atoms of elements in substances on and just under the surface of a target material are uniquely characteristic, allowing the elemental compositions of the substances to be determined.

Referring back to FIG. 2, X-ray detector 28 is positioned directly above the exposed region of the frontside surface of semiconductor wafer 30. X-ray detector 28 receives characteristic secondary X-ray photons and scattered primary X-ray photons, and produces an output signal which represents the energy levels of detected X-ray photons. Computer system 30 is coupled to receive and process the output signals produced by X-ray detector 28. An energy range of interest, which includes the energy levels of primary X-ray photons and secondary X-ray photons emitted by expected elements, is divided into several energy subranges. Computer 30 maintains counts of the number of X-ray photons detected within each subrange. After a predetermined exposure time, computer system 30 stops receiving and processing output signals and produces a graph of the counts associated with each subrange.

Figure 5:
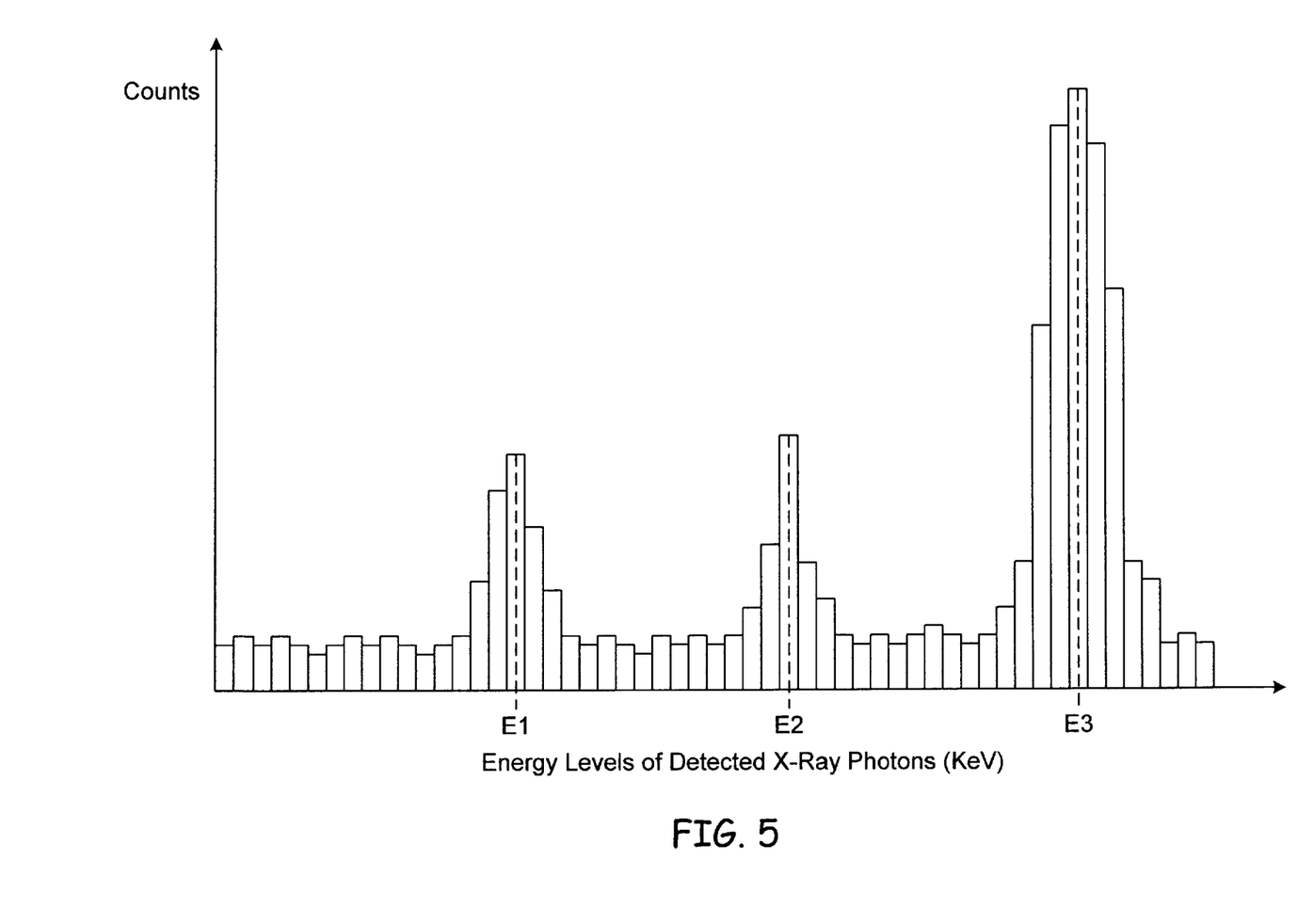

FIG. 5 is a representative graph of the counts associated with each subrange. Such a graph is basically a histogram representing the frequency distribution of the energy levels of detected X-ray photons, and is called a spectral pattern. Peaks in the frequency distribution (i.e., relatively high numbers of counts) occur at energy levels of scattered primary X-ray photons (E3) and at predominant characteristic emission energy levels (E1 and E2) of atoms of elements located on and just under the frontside surface of semiconductor wafer 32 within the exposed region. The peak in the frequency distribution occurring at energy levels of scattered primary X-ray photons (E3) is basically ignored. Energy levels E1 and E2 associated with the other two peaks in the frequency distribution are used to identify the one or more elements present on and just under the exposed region of the frontside surface of semiconductor wafer 32 according to well-known XRF methods.

A primary X-ray photon incident upon a target material may be absorbed or scattered. Characteristic secondary X-ray photons are emitted only when primary X-ray photons are absorbed. Primary X-ray photons may loose energy when scattered by atoms of the target material. Such scattered primary X-ray photons which reach the X-ray detector of an XRF instrument create an unwanted background intensity level which secondary X-ray photons must exceed in order to be discerned. Thus the smallest amount of an element which may be detected in a sample using an XRF instrument is largely determined by the background intensity level at the energy level (or corresponding wavelength) associated with characteristic secondary X-ray photons emitted by that element. The sensitivity of an XRF instrument is thus largely dependent upon the background intensity level, and the sensitivity of an XRF instrument may be improved by reducing the amount of scattered primary X-ray photons reaching the detector.

Total reflection X-ray fluorescence (TXRF) is an XRF technique ideally suited for the examination of semiconductor wafers and other materials with substantially planar surfaces. In TXRF, an angle of incidence formed between an incident primary X-ray beam and a substantially planar sample surface is very small, typically less than 0.2 degree. At such small angles of incidence, almost all of the primary X-ray photons striking the sample surface are reflected away from the surface. Primary X-ray photons are also reflected away from an X-ray detector positioned over the region of the wafer surface where the primary X-ray beam impacts the wafer surface. The number of scattered primary X-ray photons reaching the detector is thus significantly reduced. As a result, surface analysis instruments employing TXRF techniques have reduced background intensity levels over other types of XRF analysis instruments. Smaller quantities of elements may be detected with TXRF instruments due to their greater sensitivities.

It would thus be desirable to have a surface roughness measurement technique based upon the scattering of X-ray photons from the surface of a target material. Such a surface roughness measurement technique would be relatively fast and inexpensive, would be non-contact, and would also be non-destructive. Such a surface roughness measurement technique could be used to determine the qualities of oxides formed upon product wafers, and would be well suited for use in high-volume manufacturing environments.

SUMMARY OF THE INVENTION

The problems outlined above are in large part solved by an apparatus and method using XRF techniques to determine the roughness of a target surface. The apparatus includes an X-ray source and an X-ray detector. The X-ray source produces primary X-ray photons. The primary X-ray photons form a primary X-ray beam, and the primary X-ray beam is directed to and incident upon the target surface. The X-ray detector is positioned to receive primary X-ray photons scattered by the target surface. A fraction of the primary X-ray photons scattered by the target surface is directly proportional to the roughness of the target surface. The roughness of the target surface is determined from the number of primary X-ray photons scattered by the target surface and received by the X-ray detector within a predetermined exposure time.

In one embodiment, the apparatus also includes a sample stage, a displacement sensor, a position control unit, and a computer system. The target material to be analyzed is placed upon the sample stage. The displacement sensor produces a displacement signal reflecting the distance between a surface of the target material (i.e., the target surface) and the X-ray detector. The position control unit receives the displacement signal and issues a position control signal to the sample stage. The sample stage positions the target material relative to the incident primary X-ray beam in response to the position control signal. The X-ray detector produces an output signal proportional to the energy level of each received X-ray photon. The computer system receives the output signal produced by the X-ray detector and produces a histogram representing the frequency distribution of the energy levels of received X-ray photons. The computer system also uses calibration data to determine the roughness of the target surface from the number of primary X-ray photons scattered by the target surface and received by the X-ray detector within the predetermined exposure time.

The present method includes dividing up an energy range of interest, which includes the energy levels of scattered primary X-ray photons, into several segments. The X-ray detector is placed adjacent to the target surface such that the X-ray detector is oriented to receive primary X-ray photons scattered from the target surface. The target surface is then exposed to the primary X-ray beam produced by the X-ray source. The output signals produced by the X-ray detector are then recorded by incrementing counts associated with each segment of the energy range of interest. A histogram representing the frequency distribution of the energy levels of X-ray photons received by the X-ray detector is then formed by plotting the counts associated with each segment of the energy range of interest versus the energy levels of the received X-ray photons. One or more characteristics of a peak occurring in the histogram and corresponding to energy levels of scattered primary X-ray photons are used to determine the roughness of the target surface. Candidate characteristics of the peak include a maximum count associated with a segment of the energy range of interest occurring within the peak, and the area under the peak.

BRIEF DESCRIPTION OF THE DRAWINGS

Other objects and advantages of the invention will become apparent upon reading the following detailed description and upon reference to the accompanying drawings in which:

FIG. 5 is a representative graph of counts associated with each subrange of an energy range of interest produced by a computer system of the typical XRF spectroscopy apparatus of FIG. 2, wherein peaks (i.e., relatively high numbers of counts) occur at energy levels of scattered primary X-ray photons (E3) and at predominant characteristic emission energy levels (E1 and E2) of atoms of elements located on and just under the frontside surface of the semiconductor wafer, and wherein the peak occurring at energy levels of scattered primary X-ray photons (E3) is basically ignored, and wherein energy levels E1 and E2 associated with the other two peaks in the frequency distribution are used to identify the one or more elements present on and just under an exposed region of the frontside surface of the semiconductor wafer according to well-known XRF methods;

FIG. 7 is a representative graph of counts associated with segments of an energy range of interest produced by a computer system of the apparatus of FIG. 6, wherein peaks occur at energy levels of scattered primary X-ray photons (E3) and at predominant characteristic emission energy levels (E1 and E2) of atoms of elements located on and just under the frontside surface of the semiconductor wafer, and wherein one or more characteristics of the peak occurring at energy levels of scattered primary X-ray photons (E3) are used to determine the roughness of the surface of the target material within the exposed region, and wherein energy levels E1 and E2 associated with the other two peaks in the frequency distribution may be used to identify the one or more elements present on and just under an exposed region of the frontside surface of the semiconductor wafer according to well-known XRF methods.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 6:
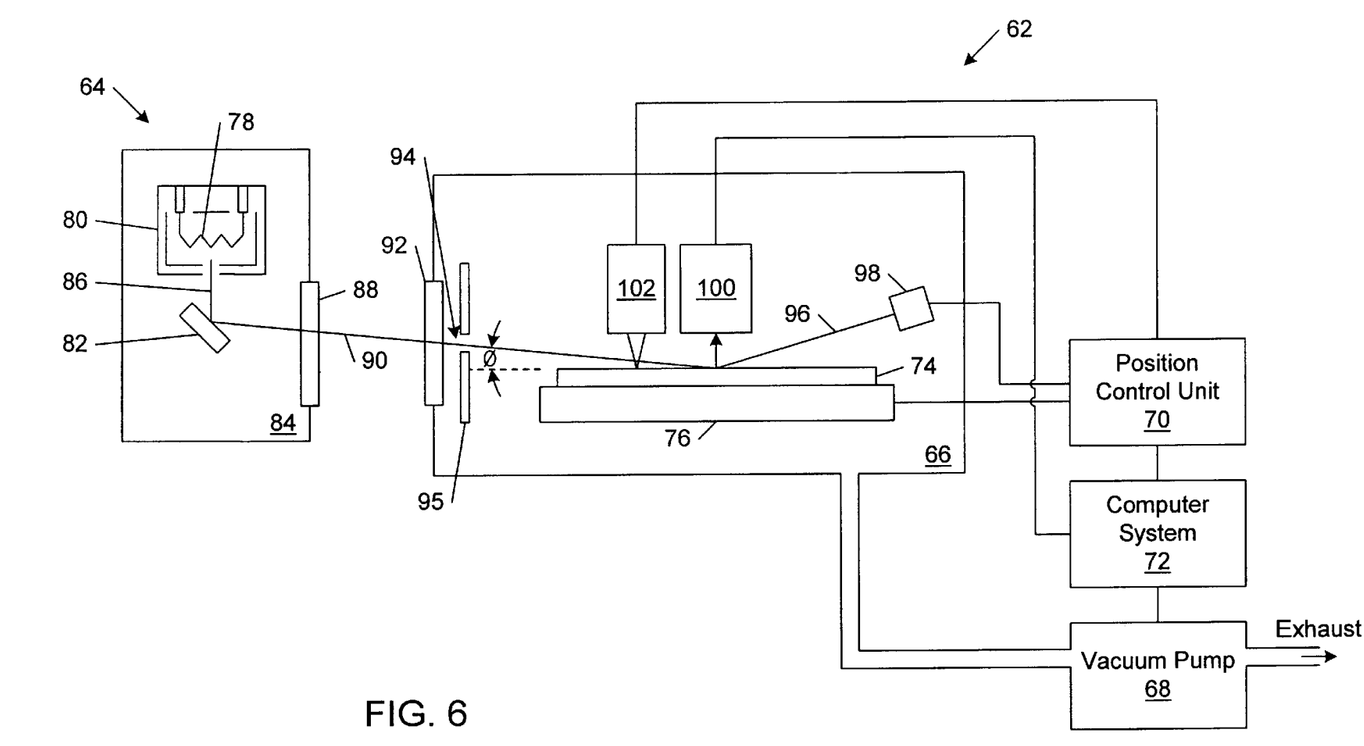
FIG. 6 is a side elevation view of an exemplary embodiment of an apparatus for measuring the roughness of a surface of a target material in accordance with the present invention, wherein the apparatus includes an X-ray source and an X-ray detector, and wherein the X-ray source produces a beam of primary X-ray photons, and wherein the beam of primary X-ray photons is directed to and incident upon a target surface, and wherein the X-ray detector is positioned to receive primary X-ray photons scattered by the target surface.

FIG. 6 is a side elevation view of an exemplary embodiment of an apparatus 62 for measuring the roughness of a surface of a target material in accordance with the present invention. Apparatus 62 includes an X-ray source 64, sample chamber 66, vacuum pump 68, a position control unit 70, and a computer system 72. In the embodiment shown, the target material is a semiconductor wafer 74. A planar backside surface of semiconductor wafer 74 is placed upon a flat upper surface of a sample stage 76 located within sample chamber 66, allowing a planar frontside surface of semiconductor wafer 44 to be exposed to primary X-ray photons during analysis.

Due to the nature of the present measurement technique, X-ray source 64 need not produce a relatively large number of X-ray photons per unit time. In the embodiment of FIG. 6, X-ray source 64 is an X-ray tube, and includes a tungsten filament 78, a cathode 80, and an anode 82 located within an evacuated chamber 84. During operation, an electric current is passed through tungsten filament 78 so as to heat tungsten filament 78 to incandescence. In this state, tungsten filament 78 gives off electrons through the process of thermionic emission. Anode 82 is fixed in place and held at ground potential during operation. Cathode 80 is charged to a highly negative potential in reference to anode 82. An electron beam 86 is formed as electrons are accelerated toward anode 82 in the electric field generated between cathode 80 and anode 82. As the highly accelerated electrons strike electrons within atoms of anode 82 and lose kinetic energy, X-ray photons are emitted from anode 82 and exit through a beryllium window 88 located in a wall of chamber 84. Chamber 84 is evacuated in order to reduce absorption of long wavelength X-ray photons within chamber 84. X-ray photons escape chamber 84 through beryllium window 88, forming primary X-ray beam 90.

Where a surface roughness measurement is to be combined with elemental analysis, the one or more materials comprising anode 82 may be chosen such that X-ray photons with sufficient energy (i.e., sufficiently short wavelengths) are produced which are able to cause atoms of elements of interest located on and just under the surface of semiconductor wafer 74 to emit secondary X-ray photons. Suitable anode materials include gold, tungsten, molybdenum, and chromium. It is noted that X-ray source 64 may also be a radioisotope source (e.g., $^{55}$Fe, $^{109}$Cd, $^{241}$Am, etc.). The X-ray photons produced by X-ray source 64 may have different energy levels and corresponding wavelengths (i.e., polychromatic) or substantially the same energy levels and corresponding wavelengths (i.e., monochromatic). For example, X-ray tubes are typically polychromatic X-ray sources, while many radioisotope sources are monochromatic.

Primary X-ray beam 90 enters sample chamber 66 through a beryllium window 92 in a wall of sample chamber 66. Substantially all of the air molecules within sample chamber 66 are evacuated prior to and during operation using a vacuum pump 68 in order to reduce absorption of long wavelength X-ray photons within sample chamber 66. Once inside sample chamber 66, a portion of primary X-ray beam 90 passes through an aperture 94 in a baffle plate 95.

Aperture 94 limits the cross-sectional area of primary X-ray beam 90. Primary X-ray beam 90 is thus redefined as it passes through aperture 94, and aperture 94 determines the size and shape of an exposed region on the frontside surface of semiconductor wafer 74 where primary X-ray photons of primary X-ray beam 90 strike the frontside surface of semiconductor wafer 74. A portion of the primary X-ray photons of X-ray beam 90 which strike the frontside surface of semiconductor wafer 74 within the exposed region are reflected away from the surface, forming a reflected primary X-ray beam 96. An X-ray sensor 98 receives reflected primary X-ray beam 96 and produces an intensity signal which reflects the relative intensity of reflected primary X-ray beam 96.

A primary X-ray photon incident upon the frontside surface of semiconductor wafer 74 may be absorbed or scattered. Primary X-ray photons may loose energy when scattered by atoms of elements on and just under the region of the frontside surface of semiconductor wafer 74. Atoms of elements on and just under the region of the frontside surface of semiconductor wafer 74 may absorb a fraction of the incident primary X-ray photons and emit characteristic secondary X-ray photons. Characteristic secondary X-ray photons are emitted only when primary X-ray photons are absorbed. An X-ray detector 100 positioned directly above and in close proximity to (i.e., adjacent to) the exposed region of the frontside surface of semiconductor wafer 74 receives scattered primary X-ray photons and any characteristic secondary X-ray photons emitted by atoms of elements upon and within the exposed region of semiconductor wafer 74. X-ray detector 100 produces an output signal proportional to the energy levels of detected X-ray photons. X-ray detector 100 may be, for example, a scintillation detector such as a thallium-doped sodium iodide crystal, designated NaI(Tl). Alternately, X-ray detector 100 may be a lithium-drifted silicon detector, designated Si(Li).

Sample stage 76 is moveable within physical limits along three orthogonal axes x, y, and z, where the x and y axes are in the horizontal plane and the z axis is normal to the horizontal plane. Sample stage 76 is coupled to receive a sample stage position control signal produced by position control unit 70, and is configured to position semiconductor wafer 74 relative to primary X-ray beam 90 and X-ray detector 100 based upon the sample stage position control signal.

As TXRF techniques produce lower background intensity levels which allow lower detection limits for simultaneous elemental analysis, TXRF techniques are preferred. An angle of incidence θ is formed between primary X-ray beam 90 and the planar frontside surface of semiconductor wafer 74. Angle of incidence θ is measured in a plane containing primary X-ray beam 90 and normal to the frontside surface of semiconductor wafer 74. In keeping with TXRF techniques, angle of incidence θ is very small, typically less than 0.2 degree. At such angles of incidence, almost all of the primary X-ray photons making up primary X-ray beam 90 and striking the exposed frontside surface of semiconductor wafer 74 are reflected away from the frontside surface.

Position control unit 70 is coupled to receive the intensity signal produced by X-ray sensor 98. In a TXRF operating mode, position control unit 70 is configured to produce the sample stage position control signal based upon the intensity signal such that the frontside surface of semiconductor wafer 74 is positioned relative to primary X-ray beam 90 for maximum reflectance of primary X-ray beam 90 from the frontside surface.

A displacement sensor 102 attached to X-ray detector 100 allows precise and automatic positioning of X-ray detector 100 relative to the exposed region of the frontside surface of semiconductor wafer 74 during operation. Displacement sensor 102 produces an output displacement signal which is proportional to the distance between a planar sensing surface of X-ray detector 100 and the frontside surface of semiconductor wafer 74. Suitable displacement sensors use incident and reflected light or sound to determine the displacement between two surfaces.

In order to facilitate the loading and unloading of semiconductor wafer 74 from sample stage 76, and to allow X-ray detector 100 to be positioned in close proximity to an exposed region of the frontside surface of semiconductor wafer 74 during operation, X-ray detector 100 and sample stage 76 move relative to one another. In a preferred embodiment, X-ray detector 100 remains stationary, and sample stage 76 is configured to move relative to X-ray detector 100 such that all areas of the frontside surface of semiconductor wafer 74 may be positioned directly under X-ray detector 100 during operation. Position control unit 70 is coupled to receive the displacement signal produced by displacement sensor 102, along with a desired sample stage position signal produced by computer system 72, and is configured to produce the sample stage position control signal derived from the displacement signal and the desired sample stage position signal.

In the embodiment of FIG. 6, the target surface is the frontside surface of a semiconductor wafer. It is noted that the target surface may be any surface, and need not be substantially planar in order to apply the present method. The target surface is, however, preferably substantially planar such that TXRF techniques may be applied. It is also noted that the target surface may be a surface of a homogeneous material, or a layer of a material formed over another material. For example, the target surface may be the surface of a metal plate, or the surface of an oxide layer formed upon a semiconductor wafer.

Computer system 72 receives the output signal produced by X-ray detector 100. An energy range of interest, which includes the energy levels of scattered primary X-ray photons and any secondary X-ray photons emitted by expected elements, is defined and divided into several equally-sized subranges or segments. Computer system 72 maintains counts of the number of X-ray photons detected within each segment. Each time the output signal produced by X-ray detector 100 corresponds to an energy level which falls within a given segment, computer system 72 increments the contents of a memory location (i.e., a count) associated with that segment. After a predetermined exposure time, computer system 72 stops receiving output signals and produces a graph of the counts associated with each segment.

Figure 7:
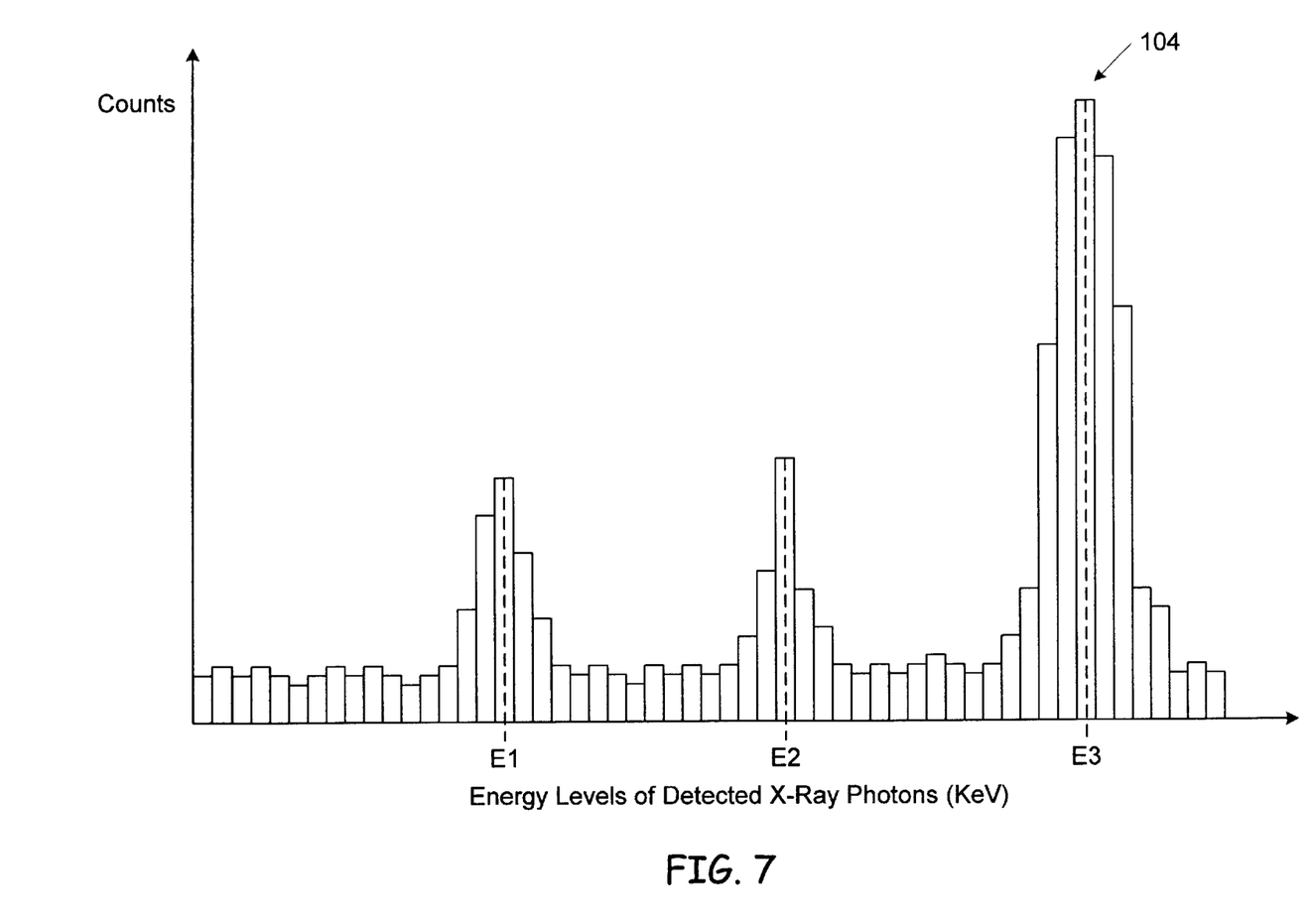

FIG. 7 is a representative graph of the counts associated with each segment of the energy range of interest. Such a graph is basically a histogram representing the frequency distribution of the energy levels of detected X-ray photons, and is called a spectral pattern. Three peaks in the frequency distribution (i.e., relatively high numbers of counts) appear in FIG. 7. The largest peak, labeled 104, occurs at energy levels of scattered primary X-ray photons (E3). Two smaller peaks occur at lower energy levels which are predominant characteristic emission energy levels (E1 and E2) of atoms of elements located on and just under the frontside surface of semiconductor wafer 32 within the exposed region.

In elemental analysis, the common use of XRF spectroscopy, peak 104 corresponding the energy levels of scattered primary X-ray photons is largely ignored. However, the present apparatus and method use one or more selected characteristics of peak 104 (e.g., the maximum count associated with peak 104, the area under peak 104, etc.) to determine the roughness of the target surface. A fraction of the primary X-ray photons scattered by the target surface is directly proportional to the roughness of the target surface, and the number of scattered primary X-rays received by X-ray detector 100 within the exposure time is directly proportional to the roughness of the target surface. That is to say the rougher the target surface, the larger the fraction of incident primary X-ray photons scattered by the target surface, and the greater the number of scattered primary X-ray photons received by X-ray detector 100 within the exposure period. The one or more selected characteristics of peak 104 are proportional to the number of scattered primary X-rays received by X-ray detector 100 within the exposure time. Thus, in effect, apparatus 62 and the present method determine the roughness of the target surface from the number of primary X-ray photons scattered by the target surface and received by the X-ray detector within the exposure time. In addition, energy levels E1 and E2 associated with the other two peaks in the frequency distribution may be used to identify the one or more elements present on and just under the exposed region of the frontside surface of semiconductor wafer 74 according to well-known XRF methods.

In addition to the graph of the counts associated with each segment of the X-ray photon energy range of interest, computer system 72 also produces a value which specifies the roughness of the target surface (e.g., the roughness of the frontside surface of semiconductor wafer 74 within the exposed region). Such surface roughness values are preferably expressed as root-mean-square (RMS) values. A calibration operation is preferably performed in order to determine the correlation between the roughness of the target surface and the one or more selected characteristics of peak 104 (e.g., the maximum count associated with peak 104, the area under peak 104, etc.). For example, target surfaces having varying degrees of surface roughness may be subjected to the present method using apparatus 62, then to an accepted surface roughness measurement technique such as AFM. A correlation between the one or more selected characteristics of peak 104 and the AFM results may then be determined. For example, an equation may be developed which expresses the relationship between the one or more selected characteristics of peak 104 and the surface roughness measurements obtained using AFM. This equation may then be used to relate achieved characteristics of peak 104 to corresponding surface roughness values.

Once apparatus 62 has been calibrated, the roughness of a target surface may be determined as follows. A region of the target surface (e.g., the frontside surface of semiconductor wafer 74) is exposed to the beam of primary X-ray photons 90 produced by X-ray source 64. X-ray detector 100, positioned in close proximity to the exposed region, detects scattered primary X-ray photons and any secondary X-ray photons emitted by atoms of elements on or just under the target surface within the exposed region. Computer system 96 receives output signals produced by X-ray detector 100 and increments corresponding counts associated with segments of the energy range of interest as described above. After a predetermined exposure time, computer system 72 stops receiving output signals and produces a graph of the counts associated with each segment. Computer system 72 also reviews the counts associated with peak 104 corresponding to the energy levels of the scattered primary X-ray photons. Computer system 72 computes the selected characteristics of peak 104 (e.g., the maximum count associated with peak 104, the area under peak 104, etc.), uses the equation determined during calibration to compute a surface roughness value, and produces the surface roughness value.

It will be appreciated by those skilled in the art having the benefit of this disclosure that this invention is believed to be an apparatus and method capable of measuring the roughness of a surface of a target material based upon the scattering of incident X-ray photons. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. An apparatus for determining the roughness of a target surface, comprising:
    an X-ray source adapted to produce a plurality of primary X-ray photons, wherein said plurality of primary X-ray photons forms a primary X-ray beam, and wherein said primary X-ray beam is incident upon the target surface;
    an X-ray detector positioned to receive primary X-ray photons scattered by the target surface, wherein the X-ray detector is adapted to produce a detector output signal proportional to energy levels of received X-ray photons; and
    a computer system coupled to receive the detector output signal and adapted to determine the roughness of the target surface based upon the number of primary X-ray photons scattered by the target surface and received by the X-ray detector within a predetermined exposure time.

2. The apparatus as recited in claim 1, wherein the target surface is a surface of a target material, and wherein the apparatus further comprises:
    a displacement sensor adapted to produce a displacement signal reflecting the distance between the target surface and the X-ray detector;
    a position control unit coupled to receive said displacement signal and adapted to produce a position control signal, wherein the position control signal is dependent upon the displacement signal; and
    a sample stage upon which the target material is placed, wherein the sample stage is coupled to receive said position control signal and adapted to position the target material relative to the incident primary X-ray beam and the X-ray detector in response to the position control signal.

3. The apparatus as recited in claim 2, further comprising an X-ray sensor positioned to receive a portion of the primary X-ray beam reflected from the target surface, wherein the X-ray sensor is adapted to produce an intensity signal proportional to the relative intensity of the reflected portion of the primary X-ray beam.

4. The apparatus as recited in claim 3, wherein the position control unit is coupled to receive the intensity signal, and wherein the position control unit produces the position control signal dependent upon the intensity signal such that a selected angle of incidence between the primary X-ray beam and the target surface is achieved.

5. The apparatus as recited in claim 4, wherein the angle of incidence between the primary X-ray beam and the target surface is measured in a plane containing the primary X-ray beam and normal to the target surface, and wherein the selected angle of incidence is less than 0.2 degree.

6. The apparatus as recited in claim 1, wherein the primary X-ray beam is incident upon an exposed region of the target surface, and wherein the X-ray detector is positioned adjacent to the exposed region.

7. The apparatus as recited in claim 1, wherein the X-ray source comprises an X-ray tube.

8. The apparatus as recited in claim 7, wherein the X-ray tube comprises an anode selected from the group consisting of tungsten, molybdenum, and chromium.

9. The apparatus as recited in claim 1, wherein the X-ray detector is a scintillation detector.

10. The apparatus as recited in claim 1, wherein the computer system uses calibration data to determine the roughness of the target surface.

11. An apparatus for determining the roughness of a surface of a semiconductor wafer, comprising:
    an X-ray source adapted to produce a beam of primary X-ray photons, wherein said beam of primary X-ray photons is incident upon the surface of the semiconductor wafer;
    an X-ray detector positioned to receive primary X-ray photons scattered from the surface of the semiconductor wafer and adapted to produce a detector output signal proportional to energy levels of received X-ray photons;
    a displacement sensor adapted to produce a displacement signal proportional to the distance between the surface of the semiconductor wafer and the X-ray detector;
    a position control unit coupled to receive said displacement signal and adapted to produce a position control signal, wherein the position control signal is dependent upon the displacement signal;
    a sample stage upon which the semiconductor wafer is placed, wherein the sample stage is coupled to receive said position control signal and adapted to position the semiconductor wafer relative to the incident beam of primary X-ray photons and the X-ray detector in response to the position control signal; and
    a computer system coupled to receive the detector output signal produced by the X-ray detector and adapted to determine the roughness of the surface of the semiconductor wafer based upon the number of primary X-ray photons scattered by the surface of the semiconductor wafer and received by the X-ray detector within a predetermined exposure time.

12. The apparatus as recited in claim 11, wherein the X-ray detector is a scintillation detector.

13. The apparatus as recited in claim 11, wherein the primary X-ray beam is incident upon an exposed region of the surface of the semiconductor wafer, and wherein the X-ray detector is positioned adjacent to the exposed region.

14. The apparatus as recited in claim 11, further comprising an X-ray sensor positioned to receive a portion of the beam of primary X-ray photons reflected from the surface of the semiconductor wafer, wherein the X-ray sensor is adapted to produce an intensity signal proportional to the relative intensity of the reflected primary X-ray photons, and wherein the position control unit is coupled to receive the intensity signal, and wherein the position control unit produces the position control signal dependent upon the intensity signal.

15. The apparatus as recited in claim 14, wherein an angle of incidence formed between the primary X-ray beam and the surface of the semiconductor wafer is effectuated using the intensity signal, and wherein the angle of incidence is measured in a plane containing the primary X-ray beam and normal to the surface of the semiconductor wafer, and wherein the angle of incidence is less than 0.2 degree.

16. The apparatus as recited in claim 11, wherein the X-ray source comprises an X-ray tube.

17. The apparatus as recited in claim 16, wherein the X-ray tube comprises an anode selected from the group consisting of tungsten, molybdenum, and chromium.

18. A method for determining the roughness of a target surface, comprising:

positioning an X-ray detector adjacent to the target surface, wherein the X-ray detector is oriented to receive primary X-ray photons scattered from the target surface, and wherein the X-ray detector is configured to produce an output signal proportional to energy levels of received X-ray photons;

exposing the target surface to a beam of primary X-ray photons;

recording the output signals produced by the X-ray detector;

forming a histogram representing the frequency distribution of the energy levels of received X-ray photons; and using one or more selected characteristics of a peak occurring in the histogram and corresponding to energy levels of scattered primary X-ray photons to determine the roughness of the target surface.

19. The method as recited in claim 18, wherein the one or more characteristics of the peak corresponding to energy levels of scattered primary X-ray photons comprises an area under the peak.

20. The method as recited in claim 18, wherein the target surface comprises a surface of a semiconductor wafer.

21. The method as recited in claim 18, further comprising knowing a correlation between the one or more selected characteristics of the peak and the roughness of the target surface prior to forming the histogram and using the one or more selected characteristics to determine the roughness of the target surface.

22. The method as recited in claim 21, wherein the knowing comprises determining a correlation between the one or more selected characteristics of the peak and the roughness of the target surface determined using an accepted surface roughness measurement technique.

23. The method as recited in claim 22, wherein the accepted surface roughness measurement technique is atomic force microscopy (AFM).

24. The method as recited in claim 18, wherein the one or more characteristics of the peak corresponding to energy levels of scattered primary X-ray photons comprises a maximum count associated with a predetermined range of energy levels within the peak.

* * * * *